(12) United States Patent
Jain

(10) Patent No.: US 8,751,920 B2
(45) Date of Patent: Jun. 10, 2014

(54) SYSTEM AND METHOD FOR IMAGE PROCESSING WITH ASSIGNMENT OF MEDICAL CODES

(75) Inventor: Vardhman Jain, Chennai (IN)

(73) Assignee: Perot Systems Corporation, Plano, TX (US)

( * ) Notice: Subject to any disclaimer, the term of this patent is extended or adjusted under 35 U.S.C. 154(b) by 1459 days.

(21) Appl. No.: 11/957,759

(22) Filed: Dec. 17, 2007

(65) Prior Publication Data

US 2009/0109239 A1   Apr. 30, 2009

(30) Foreign Application Priority Data

Oct. 30, 2007   (IN) .............. 2269/DEL/2007

(51) Int. Cl.
   *G06F 12/00*   (2006.01)
(52) U.S. Cl.
   USPC .......................................... 715/232; 715/230
(58) Field of Classification Search
   USPC ................. 715/230, 231, 232, 233, 234, 200; 705/2, 3
   See application file for complete search history.

(56) References Cited

U.S. PATENT DOCUMENTS

| | | | |
|---|---|---|---|
| 5,070,478 A | 12/1991 | Abbott | |
| 5,265,010 A | 11/1993 | Evans-Paganelli et al. | |
| 5,325,293 A * | 6/1994 | Dorne | 705/2 |
| 5,483,443 A * | 1/1996 | Milstein et al. | 705/3 |
| 5,638,505 A | 6/1997 | Hemenway et al. | |
| 5,794,208 A | 8/1998 | Goltra | |
| 5,809,476 A * | 9/1998 | Ryan | 705/2 |
| 5,832,450 A | 11/1998 | Myers et al. | |
| 6,201,539 B1 | 3/2001 | Miller et al. | |
| 6,701,508 B1 | 3/2004 | Bartz et al. | |
| 6,785,410 B2 * | 8/2004 | Vining et al. | 382/128 |
| 6,915,254 B1 * | 7/2005 | Heinze et al. | 704/9 |
| 7,409,354 B2 * | 8/2008 | Putnam et al. | 705/2 |
| 7,610,192 B1 * | 10/2009 | Jamieson | 704/9 |
| 2002/0007285 A1 * | 1/2002 | Rappaport | 705/2 |
| 2002/0138512 A1 | 9/2002 | Buresh et al. | |
| 2003/0083903 A1 * | 5/2003 | Myers | 705/2 |
| 2004/0117206 A1 * | 6/2004 | Steinberger et al. | 705/2 |
| 2004/0204961 A1 * | 10/2004 | Rensimer et al. | 705/2 |
| 2005/0137910 A1 * | 6/2005 | Rao et al. | 705/3 |
| 2007/0266304 A1 * | 11/2007 | Fletcher et al. | 715/500.1 |
| 2009/0024922 A1 * | 1/2009 | Markowitz et al. | 715/716 |
| 2010/0171682 A1 * | 7/2010 | Chen | 345/55 |

* cited by examiner

*Primary Examiner* — Stephen Hong
*Assistant Examiner* — Gregory J Vaughn
(74) *Attorney, Agent, or Firm* — Winstead PC

(57) ABSTRACT

A method of adding information to a displayed electronic image includes receiving a search request based on information from the displayed electronic image, locating at least one information responsive to the search request, and receiving identification of a selected information of the at least one information. The method also includes receiving selection of a position on the displayed electronic image at which the selected information is to be added and adding the selected information at the position on the displayed electronic image.

15 Claims, 15 Drawing Sheets

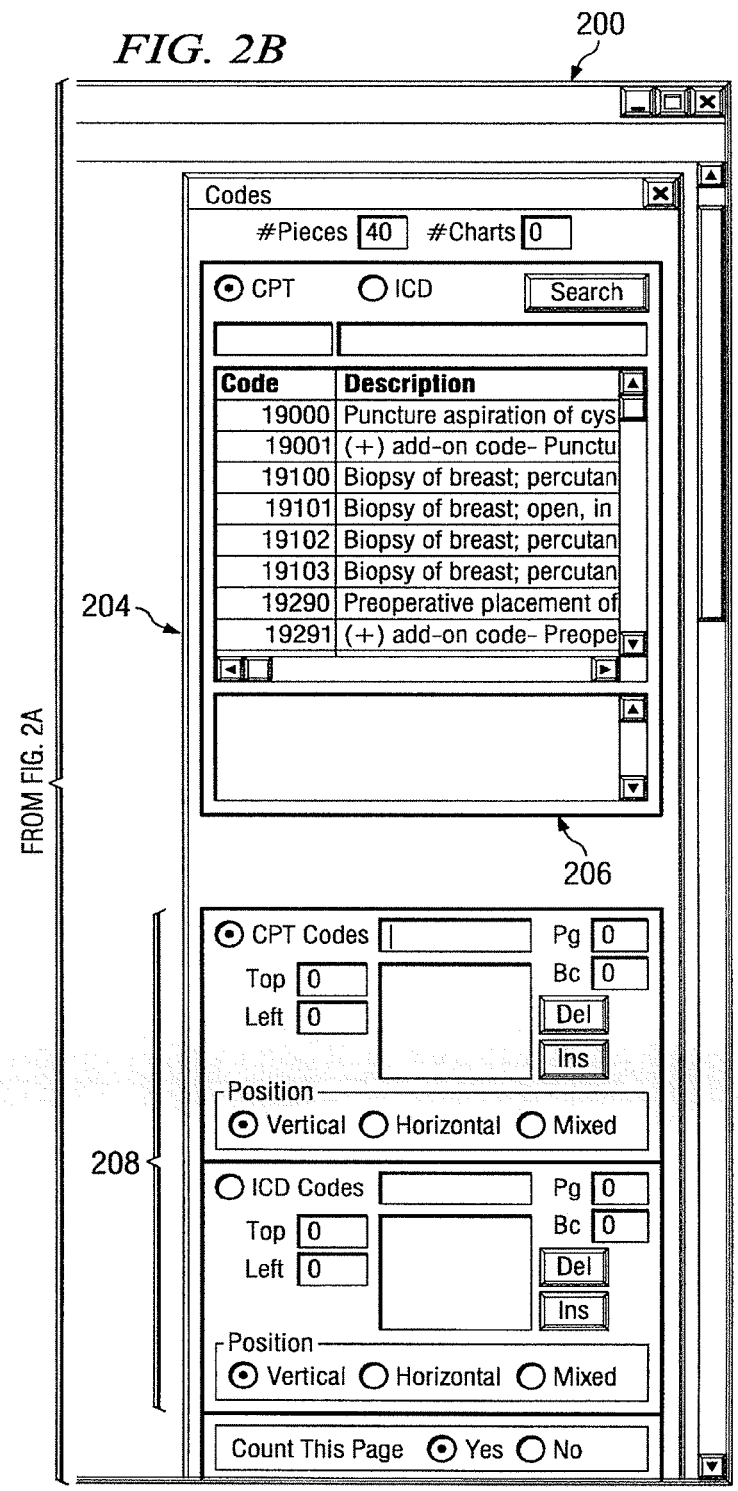

```
VCode - d:\Tiffiles\FOL_CHG03061901.tif
File  Setup  View  Print  Help
[toolbar icons] R [icons] |◄ ◀ ▶ ▶| X [  ] 14 Go
```

| NASHOBA VALLEY MEDICAL CENTER RADIOLOGY 200 GROTON ROAD, AYER, MA 01432 |||||
|---|---|---|---|---|
| NAME |||  SEX  F | ACCOUNT NUMBER |
| ORDERING PHYSICIAN ||  PT STATUS REG CLI | LOCATION  N. ED | MEDICAL RECORD NO. |
| ATTENDING PHYSICIAN | DATE OF BIRTH | AGE | DATE OF EXAM 06/13/2003 | RADIOLOGY NO. |

Clinical History:  NIOATURIA, R/C  RENAL STORES

EXAM#      TYPE/EXAM                          RESULT
000008508  CT/ABXRAY WITHOUT CONTRAST
000008509  CT/PELVIS W/O CONTRAST

ADDITIONAL CLINICAL HISTORY: Hematuria, annose for renal calouli.

CT SCAN OF THE ABDOMEN AND PELVIS WITHOUT CONTRAST: No prior files are available for comparison. Spiral imaging through the abdomen and pelvis was obtained without IV or oral contrast. The images extended from above the kidneys through the ayschysis pubis. The patient in status pont cholscyatactory. The visualised liver and spleen are otherwise unremarkable. The kidneys show no new lesions, hydronephrosis or calculi. What is seen of the pancreas is unremarkable. What is seen of the bladder is within the realm of normal. The patient appears status post hysterectomy. Bowel gas is near to the rectum.

IMPRESSION: NO CAUSES FOR THE PATIENT'S HEMATURIA IDENTIFIED ON THE IMAGES OBTAINED.

P: 06/17/2003  1225

REPORT SIGNATURE ON FILE 06/13/2003 
         Reported by:
         Signed by:

Technologist: Angelo Alvarez
Transcribed Date/Time:  06/18/2003 (0833)
Transcriptionist:  #1238.FB
Printed Date/Time:  06/18/2003 (0918)   Batch No.: 140

PAGE 1                    NASHOBA RADIOLOGY BILLING COPY

```
VCode - \\Bcvhs-pfree02\Coding\PAPERFREE\ams\test\FOL_CHG03071701B.tif
File  Setup  View  Print  Help
```

MEDICAL CENTER RADIOLOGY

| NAME | | | SEX | ACCOUNT NUMBER |
|---|---|---|---|---|
| | | 604 | F | |
| ORDERING PHYSICIAN | | PT STATUS RBO CLI | LOCATION N. MAM | MEDICAL RECORD NO. |
| ATTENDING PHYSICIAN | DATE OF BIRTH | AGE 50 | DATE OF EXAM 07/14/2003 | RADIOLOGY NO. |

602

Clinical History:   SCREENING MAMMO

EXAM#         TYPE/EXAM                                RESULT
000012062    MAMAC/SCREENING MAMMOGRAM    NEED ADD'L IMAGING EVAL

ADDITIONAL CLINICAL HISTORY: [Routine screening.]

[SCREENING MAMMOGRAM:] Craniocaudal and mediolateral oblique views of the breasts were obtained. Comparison is made to several prior studies. There are some areas of asymmetric breast density that are seen today that I would recommend some spot views of. These are in the outer aspect of the right breast and the medial aspect of the left breast.

IMPRESSION: NEW ASYMMETRIC BREAST DENSITIES WHEN COMPARED TO THE PREVIOUS EXAMS. [ADDITIONAL VIEWS RECOMMENDED.] PLEASE SEE THE BILATERAL MAMMOGRAM REPORT FOR FURTHER DESCRIPTION AND FINAL DISPOSITION.

THE FALSE-NEGATIVE RATE OF MAMMOGRAPHY IS APPROXIMATELY 10%. THE MAMMOGRAM SHOULD BE VIEWED AS A COMPLEMENT TO THE CLINICAL BREAST EXAM. ANY PALPABLE ABNORMALITY SHOULD BE MANAGED ON CLINICAL GROUNDS. THE RESULTS WERE SENT TO THE PATIENT.

Category 0 – needs further evaluation.

d:  07/14/2003  1523

REPORT SIGNATURE ON FILE 07/15/2003 
Reported by:
Signed by:

TO FIG. 6B

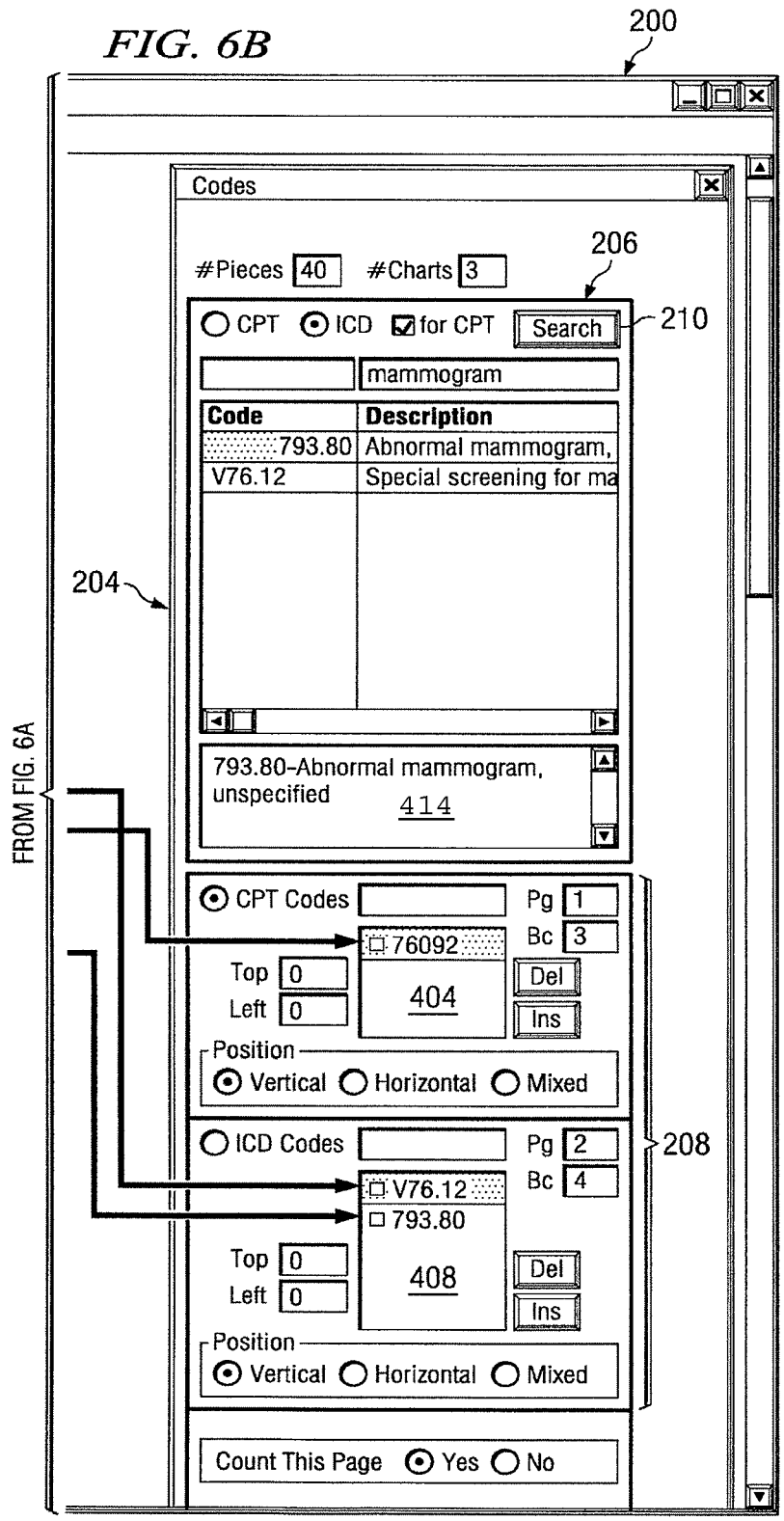

FIG. 7A

```
VCode - \\Bcvhs-pfree02\Coding\PAPERFREE\ams\test\FOL_CHG03071701B.tif
File  Setup  View  Print  Help
[toolbar icons] R [icons] [29] [Go]
```

| NAME | | | | SEX | ACCOUNT NUMBER |
|---|---|---|---|---|---|
| | | | | F | N0223901 |
| ORDERING PHYSICIAN | | | PT STATUS | LOCATION | MEDICAL RECORD NO. |
| | | | REG CLI | N. XRAY | N000004018 |
| ATTENDING PHYSICIAN | | DATE OF BIRTH | AGE | DATE OF EXAM | RADIOLOGY NO. |
| | | 02/18/1946 | 57 | 07/14/2003 | |

Clinical History:    FELL BACKWARDS THIS MORNING

73110

EXAM#          TYPE/EXAM                          RESULT            73080 ←
000012033   RAD/HUMERUS RIGHT 2 VIEWS                        73060
000012034   RAD/ELBOW RIGHT 2 VIEWS
000012035   RAD/WRIST RIGHT 3 VIEWS MINIMUM

ADDITIONAL CLINICAL HISTORY:   Status post fall with pain and laceration, limited motion.

RIGHT WRIST, FOUR VIEWS: Four views of the wrist show the carpus to align normally. No definite fractures are seen. There are some minor cystic changes in the lunate bone. The patient is slightly demineralized.

IMPRESSION: NO ACUTE FRACTURE IDENTIFIED.

RIGHT ELBOW: Three views of the elbow reveal the elbow joint to articulate normally. No fracture or dislocation is identified. There is no evidence of an elbow joint effusion. There is minor olecranor spurring.

IMPRESSION: NORMAL EXAMINATION OF THE ELBOW.

RIGHT HUMERUS, TWO VIEWS: Two views of the humerus show no visualized fracture. There is some spurring at the greater tuberosity of the humeral head and AC joint osteoarthritis.

IMPRESSION: NO ACUTE FRACTURE IS SEEN.                881.02
                                                                                    881.01 ←
THE RESULTS WERE CALLED TO DR. OFFICE.          881.03

FIG. 9

```
VCode - \\Bcvhs-pfree02\Coding\PAPERFREE\ams\TEST1\FOL_CHG03072102A.tif
File  Setup  View  Print  Help
```

| NAME | | | SEX<br>F | ACCOUNT<br>NUMBER |
|---|---|---|---|---|
| ORDERING PHYSICIAN | | PT<br>STATUS<br>REG CLI | LOCATION<br>N. MAM | MEDICAL<br>RECORD NO. |
| ATTENDING PHYSICIAN | DATE OF<br>BIRTH | AGE | DATE OF<br>EXAM<br>07/15/2003 | RADIOLOGY<br>NO. |

Clinical History:  ROUTINE                                  76092

EXAM#      TYPE/EXAM                       RESULT
000012172  MAMAC/SCREENING MAMMOGRAM       NEED ADD'L IMAGING EVAL

ADDITIONAL CLINICAL HISTORY: Screening.

SCREENING MAMMOGRAM: Craniocuadad and mediolateral oblique views of the breasts were obtained and compared to prior studies. In the right breast, there is a questionable ovoid density measuring 8 mm in size on the oblique view. There is some dense tissue laterally. I would recommend additional views for further evaluation of this finding.

On the left, there is a questionable area of distortion centrally on the cranial view that is not definitiely borne out on the oblique view. I would recommend some additional views to this side. The area of questionable distortion is just lateral to the stereotactic breast biopsy clip. There appear to be several benign type calcifications that appeared to be present previously and do not appear significantly changed.

IMPRESSION: ? NEW MASS ON THE RIGHT AND DISTORTION ON THE LEFT. ADDITIONAL VIEWS RECOMMENDED. PLEASE SEE THE BILATERAL MAMMOGRAM REPORT FOR FURTHER DESCRIPTION AND FINAL DISPOSITION.

THE FALSE-NEGATIVE RATE OF MAMMOGRAPHY IS APPROXIMATELY 10%. THE MAMMOGRAM SHOULD BE VIEWED AS A COMPLEMENT TO THE CLINICAL BREAST EXAM. ANY PALPABLE ABNORMALITY SHOULD BE MANAGED ON CLINICAL GROUNDS. THE RESULTS WERE SENT TO THE PATIENT.

Category 0 - needs further evaluation.                    V76.12
                                                          793.80

SYSTEM AND METHOD FOR IMAGE PROCESSING WITH ASSIGNMENT OF MEDICAL CODES

BACKGROUND

1. Technical Field

This patent application relates generally to image processing using an in-built repository of medical codes and, more particularly, but not by way of limitations, to an image-processing application with an in-built repository of medical codes that may be used to assist in lookup of appropriate international classification of diseases (ICD) and common procedure terminology (CPT) codes and assignment of the codes to scanned medical-record images.

2. History of Related Art

In today's medical-records processing environment, medical charts providing a diagnosis of and procedures performed on a patient are frequently provided by medical professionals to outside vendors in a scanned-image format (e.g., TIFF). The scanned images are typically routed to a medical-records coding team that is responsible for assigning ICD and CPT codes to the medical records. In a typical medical-record coding procedure, one software application is used for viewing the images, while another software application is used to add codes to an electronic image file. The codes are oftentimes determined via lookup in a book or manual.

In some cases, new specialty codes are not known to personnel entering the medical codes until some time after the new specialty codes become available due to delays in publication of books or manuals from which the codes are looked up. In addition, errors in code entry occur due to typographical mistakes when code-entry personnel mistype a code to be included on the medical record. In light of the above, improvements in systems and methods for determining, assigning, and adding medical-record codes to scanned-image medical records are needed.

SUMMARY OF THE INVENTION

A method of adding information to a displayed electronic image includes receiving a search request based on information from the displayed electronic image, locating at least one information responsive to the search request, and receiving identification of a selected information of the at least one information. The method also includes receiving selection of a position on the displayed electronic image at which the selected information is to be added and adding the selected information at the position on the displayed electronic image.

Logic for adding information to a displayed electronic image is encoded in computer-readable media and is operable when executed to receive a search request based on information from the displayed electronic image and to locate at least one information responsive to the search request. The logic is also operable when executed to receive identification of a selected information albeit at least one information, to receive selection of a position on the displayed electronic image at which the selected information is to be added, and to add the selected information at the position on the displayed electronic image.

A system for adding information to a displayed electronic image includes a processor operable to locate at least one information and add selected information of the at least one information to the displayed electronic image, a memory interoperably coupled to the processor, and a user interface interoperably coupled to the processor. The user interface includes a lookup display area and an imaging display area. The lookup display area is operable to display information regarding a search request based on information from the displayed electronic image and display information regarding the selected information. The imaging display area is operable to display the electronic image, display a selection of a position on the displayed electronic image at which the selected information is to be added, and display added information at the position on the displayed electronic image.

BRIEF DESCRIPTION OF THE DRAWINGS

A more complete understanding of the method and apparatus of the present invention may be obtained by reference to the following detailed description when taken in conjunction with the accompanying drawings wherein:

FIGS. 2A-B illustrate an image-processing system user interface;

FIGS. 3A-B illustrate the image-processing system user interface of FIGS. 2A-B following selection of a code to be entered and a location at which the code is to be placed;

FIGS. 6A-B illustrate the user interface of FIGS. 2A-B in a typical-use scenario;

FIGS. 7A-B illustrate the user interface with medical codes added to a medical-chart image displayed therein;

FIG. 9 illustrates a modified medical-chart image with medical codes added thereon by a medical-coding team member.

DETAILED DESCRIPTION OF ILLUSTRATIVE EMBODIMENTS OF THE INVENTION

Figure 1A:
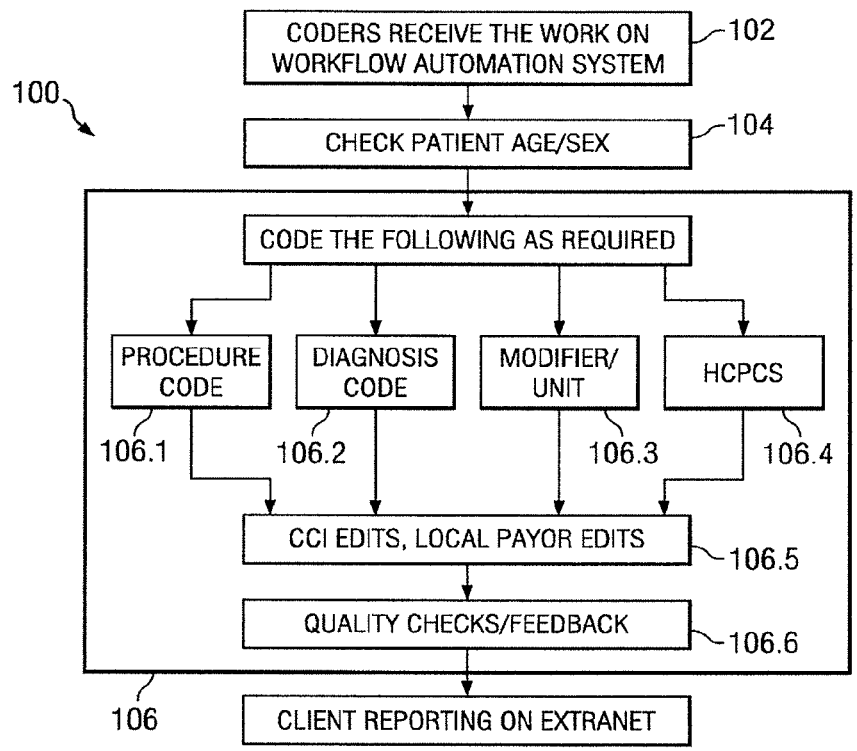
FIG. 1A illustrates an overall work flow in accordance with principles of the invention.

In various embodiments of the invention, medical-chart images describing a diagnosis of and procedures performed on a patient are provided by a medical professional to a vendor in a scanned-image format (e.g., TIFF). The images are typically routed to a medical-coding team responsible for assigning ICD and CPT codes to the medical charts. ICD and CPT codes are used for illustrative purposes throughout the disclosure of this patent application; however, those having skill in the art will appreciate that other medical-record codes, as well as information other than medical-record codes, may be used instead of ICD or CPT medical-record codes without departing from principles of the invention.

Various embodiments of the invention enable a medical-coding team member to input CPT and ICD codes and their related descriptions. The medical codes can be added to a medical-chart image directly via, for example, a click of a mouse pointer on a medical-chart image. For purposes of this patent application, the term manual selection of a position on an image means selection of the position by use of a visual indicator such as, for example, a pointer shown on a video display, as opposed, for example, to input of Cartesian coordinates on the image. If more than one CPT or ICD code is applicable to a given medical-chart image, the codes to be added can be positioned in multiple formats such as, for example, vertical, horizontal, or mixed. The vertical format causes codes to be added vertically, while the horizontal format causes the codes to be added horizontally. If the mixed format is chosen, the codes are printed one beneath the other, with a line in between. Check boxes adjacent the codes may be checked in order to select the mixed format. The checked code is added above a line separated by commas and the remaining codes following the checked codes are added below the line.

The image-processing software application also includes, in various embodiments, a search option that enables a medical-coding team member to search for various codes by entering part of a code or a description of a code. Moreover, a search function employed in various embodiments permits a medical-coding team member to more easily obtain a correct combination of CPT and ICD codes.

CPT codes are procedure codes assigned for a service provided, for example, by a physician. ICD codes correspond to a diagnosis or condition that made the patient consult or be referred to the physician. For example, an ICD code might correspond to chest pain, while a CPT code might correspond to a chest x-ray. In a typical process, in order to get a procedure code reimbursed by insurance to the physician, the ICD code chosen should prove the medical necessity. A counter employed in various embodiments counts the number of pages in a given batch and also counts the total number of pages on which codes have been added within the batch. Moreover, the number of CPT codes added, the number of ICD codes added, and the number of patients whose medical charts have been counted are counted.

The image-processing software application provides medical-coding team members with a single application for viewing medical-chart image files and assigning and publishing the codes directly on the medical-chart image files. Various embodiments provide enhanced coding accuracy by suggesting the code to be applied based on keywords defining an encounter and can evolve as new specialty codes are imported or entered. Some embodiments come with application adapters for communicating the codes to clients, for example, using XML files. In a typical embodiment, the batches are converted and uploaded as XML files in order to consume less data-storage capacity than a TIFF file. The image-processing software application may be completely integrated with a work flow management application as noted above. When such is the case, in most situations: 1) double data entry of assigned codes is avoided; 2) quality control agents can edit assigned codes published on an image file; and 3) cross-dimensional reports on specialties and service-level performance variables may be generated.

FIG. 1A illustrates an overall work flow in accordance with principles of the invention. In a typical embodiment, an image-processing software application is tightly integrated with a work flow software application. The work flow software application serves to track batches processed by the coding team. The batches picked up for processing in a work flow management system can be processed in the image-processing software application. The batches are typically integrated by a unique batch or document ID.

A medical-chart image may be tracked throughout its life cycle and quality-assurance reviews may be conducted for verification. For example, it may be verified that medical codes have been correctly entered on the medical-chart image. Integration of the image-processing software application and the work flow software application serves to keep various individuals, including, for example, a client as well as operations managers of the vendor, informed regarding productivity of medical-coding team members and also serves to quickly resolve processing bottlenecks via effective collaboration.

In FIG. 1A, a process flow 100 begins at step 102. At step 102, the medical-coding team members receive medical-chart image files on a work flow automation system. At step 104, the age and sex of the patient are verified. At step 106, image processing is initiated by the image-processing software application. Various substeps performed within step 106 are described in further detail below.

In step 106, one or more of substeps 106.1, 106.2, 106.3, and 106.4 is performed as needed. Substep 106.1 relates to procedure codes. The procedure codes of substep 106.1 report the medical, surgical, and diagnostic services performed. Substep 106.2 relates to diagnosis codes. The diagnosis codes of substep 106.2 are specific codes to report the morbidity conditions or diseases of the patient and newly-recognized conditions. The diagnosis code assigned depicts either the reason for encounter or final conclusion or diagnosis. The diagnosis code should prove the medical necessity for the procedure code assigned to get the physician service reimbursed.

Substep 106.3 deals with modifiers/units. Modifiers are two-digit codes appended along with the procedure code, whenever necessary, to indicate unusual or extra or reduced service by a physician. Modifiers denote a modified service provided by the physician as against a defined procedure service description. Some modifiers affect reimbursement. Units are generally used to denote the quantity of a service.

Substep 106.4 deals with healthcare common procedure coding system (HCPCS). Level 2 national codes are assigned when a specific CPT code is not found or may be assigned based on insurance guidelines. HCPCS is a uniform method for healthcare providers and medical suppliers to report professional services, procedures, and supplies.

From steps 106.1-106.4, execution proceeds to substep 106.5, at which substep CCI and local payor edits take place. A CCI-correct coding initiative should be verified by a coder to ensure compliance. Verification is performed whether one code is bundled into another, to sequence procedures based on relative value units (RVUs) and to verify global days for a particular procedure service. From substep 106.5, execution proceeds to 106.6, at which step quality checks and feedback regarding the preceding substeps of step 106 occur. Substep 106.6 typically involves a random or regular audit done by the supervisor of the team to ensure quality work and compliance. Any discrepancies noted and feedback are typically given to the coder.

At the completion of substep 106.6, step 106 is complete. From step 106 execution proceeds to step 108. At step 108, the coded medical-chart image is reported to the client, for example, on an extranet.

Figure 1B:
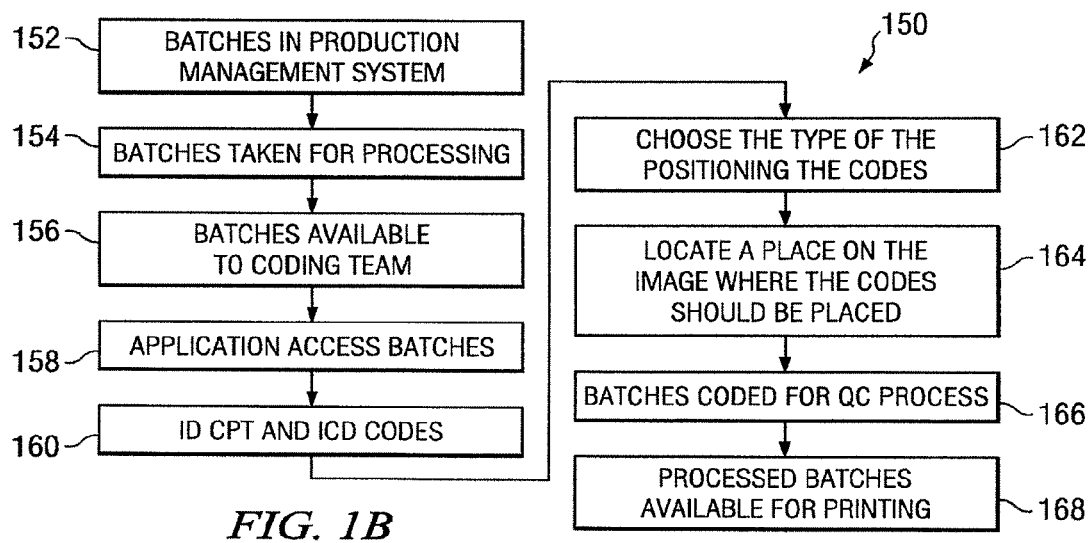
FIG. 1B illustrates an image-coding process in accordance with principles of the invention.

FIG. 1B illustrates an image-coding process in accordance with principles of the invention. An image-coding process 150 may be used by a medical-coding team to identify and add medical codes pertinent to treatment of patients to medical-chart images. The added codes may be used to enable a charge-entry team to easily process charges pertaining to the treatment, for example, by keying in the added medical codes. A medical-coding team member can identify and add various ICD and CPT codes based upon details of the medical-chart image. In a typical embodiment, an image-processing software application permits the medical codes to be added to the medical-chart image by positioning a cursor on a desired portion of the medical-chart image as displayed and clicking, for example, a mouse. The cursor identifies a location where the medical code is to be added, for example, using coordinates measured from a top edge and a leftmost edge of the medical-chart image. Various embodiments of the image-processing software application allow positioning of the medical codes to be added to the medical-chart image to be performed in various ways.

Referring again to FIG. 1B, the process 150 begins at step 152. At step 152, batches of medical-chart images are input into the workflow management system. From step 152, execution proceeds to step 154. At step 154, the medical-chart image batches are taken for processing. The batches may be processed by the coders via two different methods: 1) an auto-allocation process; and 2) a manual allocation process. In the auto-allocation process, pending documents in a queue are allocated on a random basis to all coders. In the manual allocation process, a supervisor allocates the documents to be processed to subordinates.

From step 154, execution proceeds to step 156. At step 156, the medical-chart images are made available to a medical-coding team. From step 156, execution proceeds to step 158. At step 158, the image-processing software application accesses the medical-chart image batches. From step 158, execution proceeds to step 160. At step 160, the image-processing software application is utilized by a medical-coding team member to identify CPT and ICD codes applicable to the medical-chart images in the batches. From step 160, execution proceeds to step 162. At step 162, the type and positioning of the medical codes identified at step 160 to be added to the medical-chart image are chosen by the medical-coding team member.

From step 162, execution proceeds to step 164. At step 164, the medical-coding team member locates a place on the medical-chart image where the codes are to be placed. From step 164, execution proceeds to step 166. At step 166, the medical-chart image batches are coded for a quality-control process to be performed. The quality-control process involves a quality-control member verifying details entered by the coder. The quality-control member can make any modifications needed. From step 166, execution proceeds to step 168. At step 168, the processed batches are made available for printing.

Figure 1C:
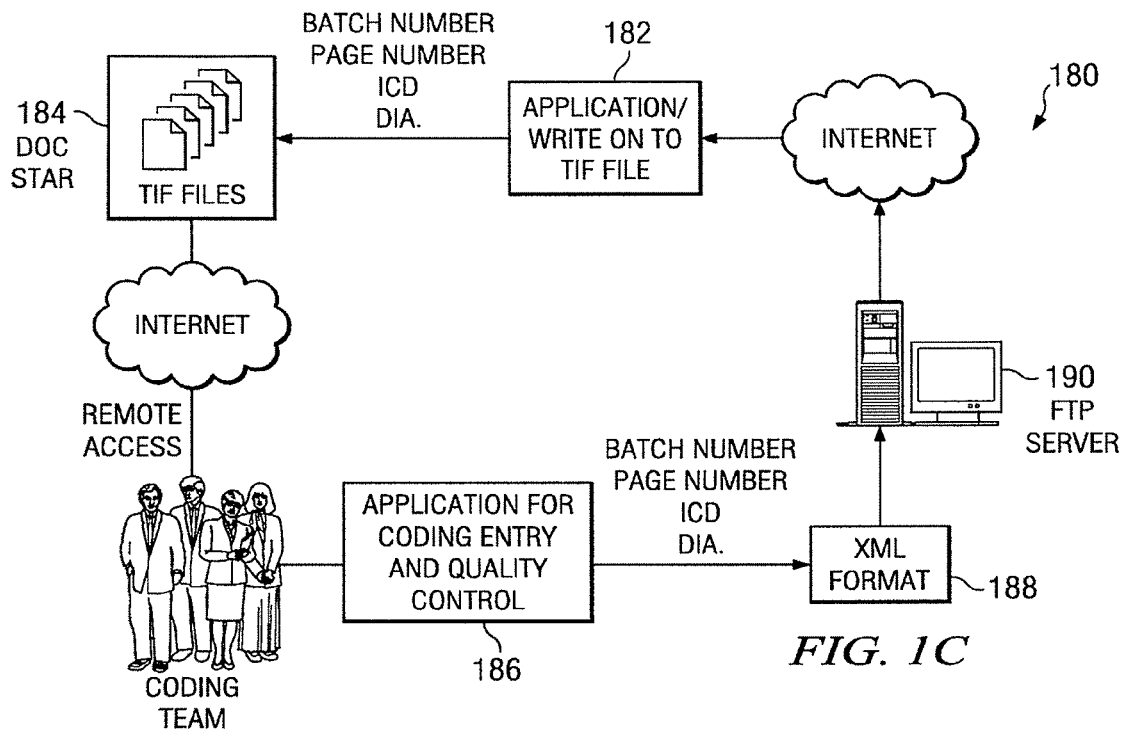
FIG. 1C illustrates an information exchange flow in accordance with principles of the invention.

FIG. 1C illustrates an information exchange flow for interfacing an image-processing software application with a client system. In a flow 180, a publishing application 182 is initially used to create medical-chart images in the form of electronic files such as, for example, .tif, .jpg, or .pdf files. The published medical-chart image file are provided to an electronic document storage and retrieval system 184, illustrated in FIG. 1C as DOC Star. Those having skill in the art will appreciate that other systems besides a DOC Star system can be used as the storage and retrieval system 184 without departing from principles of the present invention. The published documents from the publishing application 182 to the storage and retrieval system 184 are assigned a batch number, page numbers, and an ICD diagnosis.

A batch number is a unique identifier. Typical batch-number nomenclature includes client name in acronym form, date of service, and download date. The batch number permits easy identification of a particular batch from among many similar batches.

Once the medical-chart image files are located on the system 184, a medical-coding team which, in a typical embodiment, includes a plurality of members, may remotely access the storage and retrieval system 184 via, for example, the internet. The coding team may utilize, for example, an application for coding entry and quality control 186, an example of such an application being an embodiment of an image-processing software application in accordance with principles of the present invention. Following coding entry and quality control via the application for coding entry and quality control 186, edited versions of the medical-chart images processed via the application 186 are provided in, for example, XML format 188, batch number, page number, and ICD diagnosis to a server 190, which, in a typical embodiment, is a file transfer protocol (FTP) server. The medical-chart image files may then be provided to the publishing application 182 via, for example, the internet from the server 190 as indicated. The publishing application 182 then can republish the medical-chart image files.

The flow 180 is a typical way of entering medical codes into the client system. It is often important to clients to preserve their medical charts and corresponding codes from a compliance and audit perspective. A publisher XML adaptor (e.g., using the XML format 188) allows this objective to be accomplished. The client places medical-chart image files to be coded on an FTP server (e.g., the FTP server 190). The medical-coding team accesses the medical-chart image files and coding operations are performed directly on the client system. The coding team publishes the codes on the medical-chart image files and transfers the data to the client, for example, at the end of the workday using, for example, an XML-based flat data file (e.g., XML format 188). The client can use the publishing application 182 to print the added medical codes on the medical-chart image files. Thus, the client can preserve the coded medical charts in a digital format for compliance and audit.

In cases where the coding team does not have direct access to a client system, the XML records may be imported into the client system using software tools. In another option, manual entry of codes could be done. XML conversion and upload is typically done by the supervisor and then communicated to the client. Coding work is typically done by coders. In cases where the client uses a document management system for cataloging medical charts, the coding team can access the files remotely and perform coding services by entering codes into the client system.

Figure 2A:
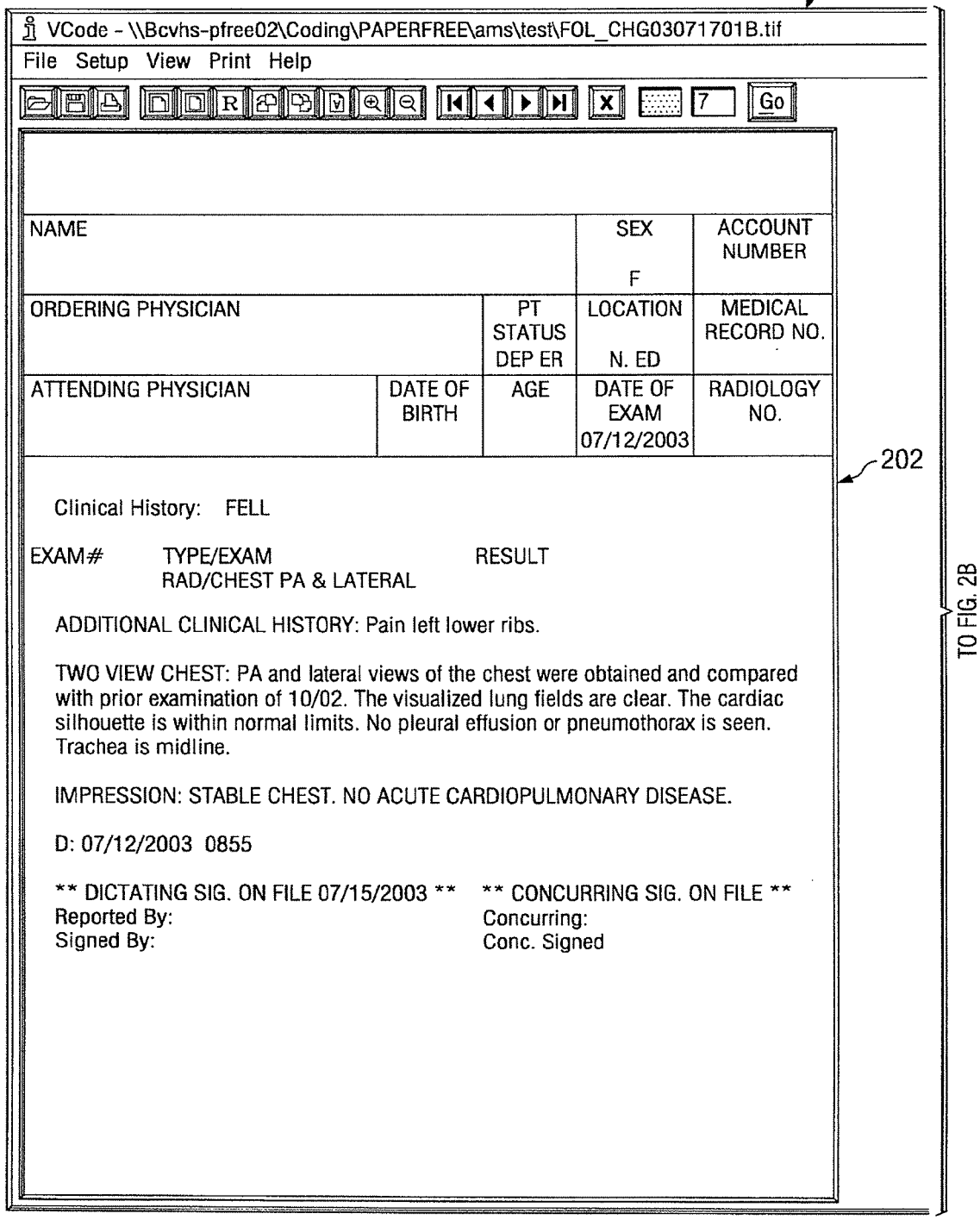

FIGS. 2A-B illustrate an image-processing system user interface of an image-processing software application in accordance with principles of the invention. In a typical embodiment, when a medical-coding team member selects a provided medical-chart image, the image-processing software application launches. A user interface 200 is, in a typical embodiment, divided into two areas: a) an imaging area 202; and b) a medical-code area 204. The imaging area 202 shows a medical-chart image. The medical-code area 204 includes a free-text search facility 206 that the medical-coding team member can use to look up appropriate ICD and CPT codes by searching by specific keywords read from the medical-chart image displayed in the imaging area 202 or by code number. As part of the free-text search facility 206, either CPT or ICD codes may be selected for search. Once the medical-coding team member selects the proper codes to be applied to the medical-chart image, the medical-coding team member can specify, via a location tool 208, location coordinates on the medical-chart image at which the chosen medical codes are to be placed.

Figure 3B:
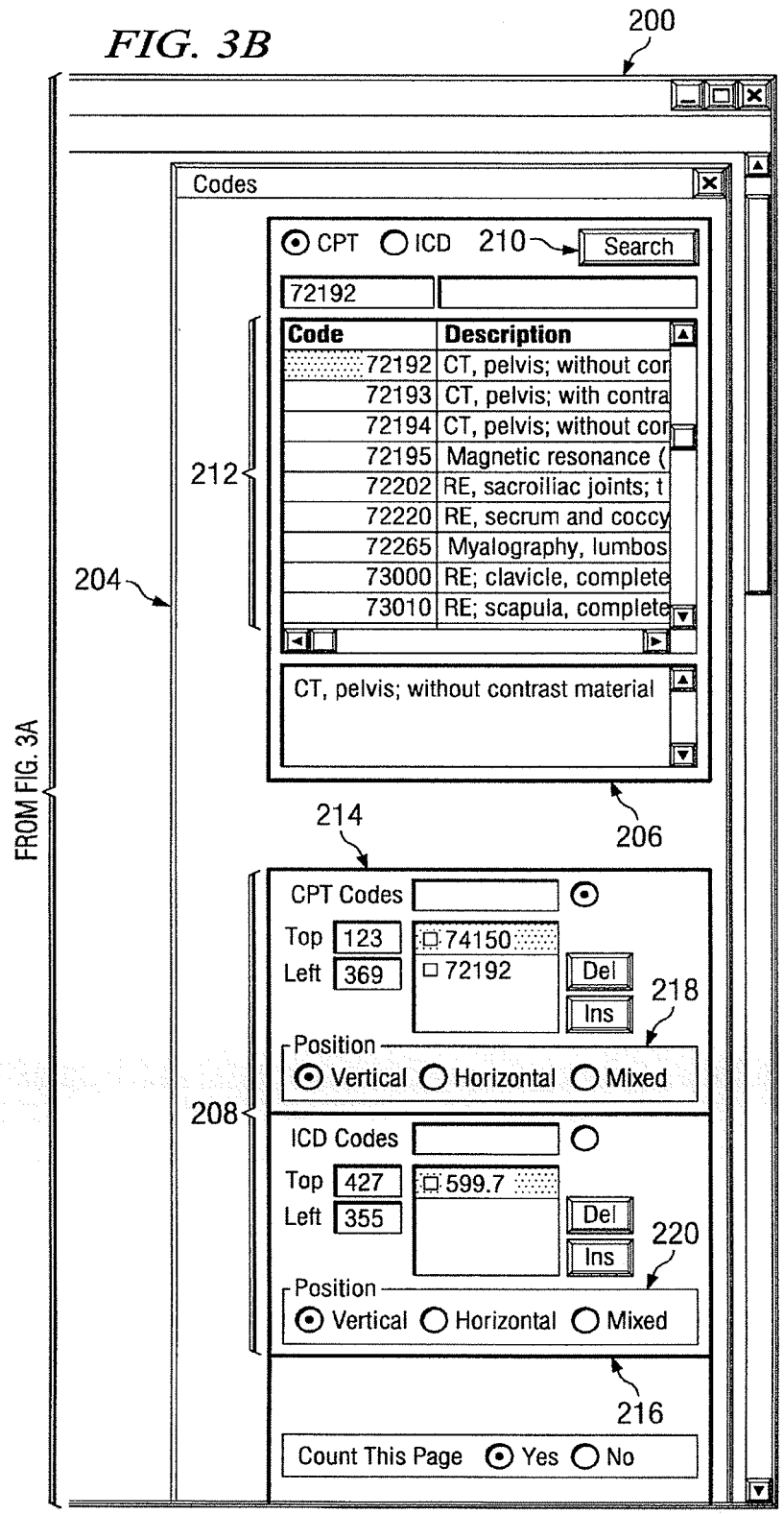

FIGS. 3A-B illustrate the image-processing system user interface following selection of medical codes to be entered and a location at which each of the medical codes is to be added. In contrast to FIGS. 2A-B, in FIGS. 3A-B, a CPT code of 72192, corresponding to a CT scan of the pelvis without contrast material, is selected for entry from within the free-text search facility 206. As will be apparent to those having skill in the art, the CPT code 72192 likely was obtained via use of the free-text search facility 206 by inputting key words from the medical-chart image as displayed in the imaging area 202 and pressing a search button 210 to yield a drop-down list of potential medical codes as illustrated within a free-text search list 212 of the free-text search facility 206.

Within the location tool 208, the CPT code 72192 and a CPT code 74150 are both illustrated as available to be placed on the medical-chart image displayed within the imaging area 202. The CPT code 74150 is bolded, which permits the medical-coding team member to browse a list of possible diagnosis codes (e.g., ICD codes) for the CPT code. Also illustrated within the location tool 208 is a CPT code 72192, which code can be selected and positioned for placement on the medical-chart image as described above. Also illustrated within the location tool 208 is an ICD code 599.7, which is available for placement on the medical-chart image displayed in the imaging area 202. In both the case of a CPT codes section 214 and an ICD codes section 216 of the location tool 208, Cartesian coordinates are utilized to position the medical codes in a portion of the medical-chart image that is blank or otherwise available for placement of the medical codes.

In the example illustrated in FIGS. 3A-B, the CPT code 74150 is selected to be placed on the medical-chart image at a position 123 units from the top of the displayed medical-chart image and 369 units from the leftmost edge of the medical-chart image. In similar fashion, the ICD code 599.7 is selected to be placed 427 units from the top of the medical-chart image and 355 units from the leftmost edge of the medical-chart image. In a typical embodiment, the units are in pixels. The units may be displayed to show where the codes are to be assigned in a particular patient record. The units can be set as default for a particular client based on a client template.

In addition, the location tool 208 includes a CPT position selector 218 and an ICD position selector 220, in each of which vertical, horizontal, or mixed formats may be selected. The vertical format causes the medical codes to be added vertically, while the horizontal format causes the codes to be added horizontally. In contrast, if the mixed format is chosen, the codes are printed one beneath the other, with a line in between. Check boxes adjacent the codes may be checked in order to select the vertical, horizontal, or mixed format. The checked code is added above a line separated by commas and the other codes following the checked codes are added below the line.

Figure 4:
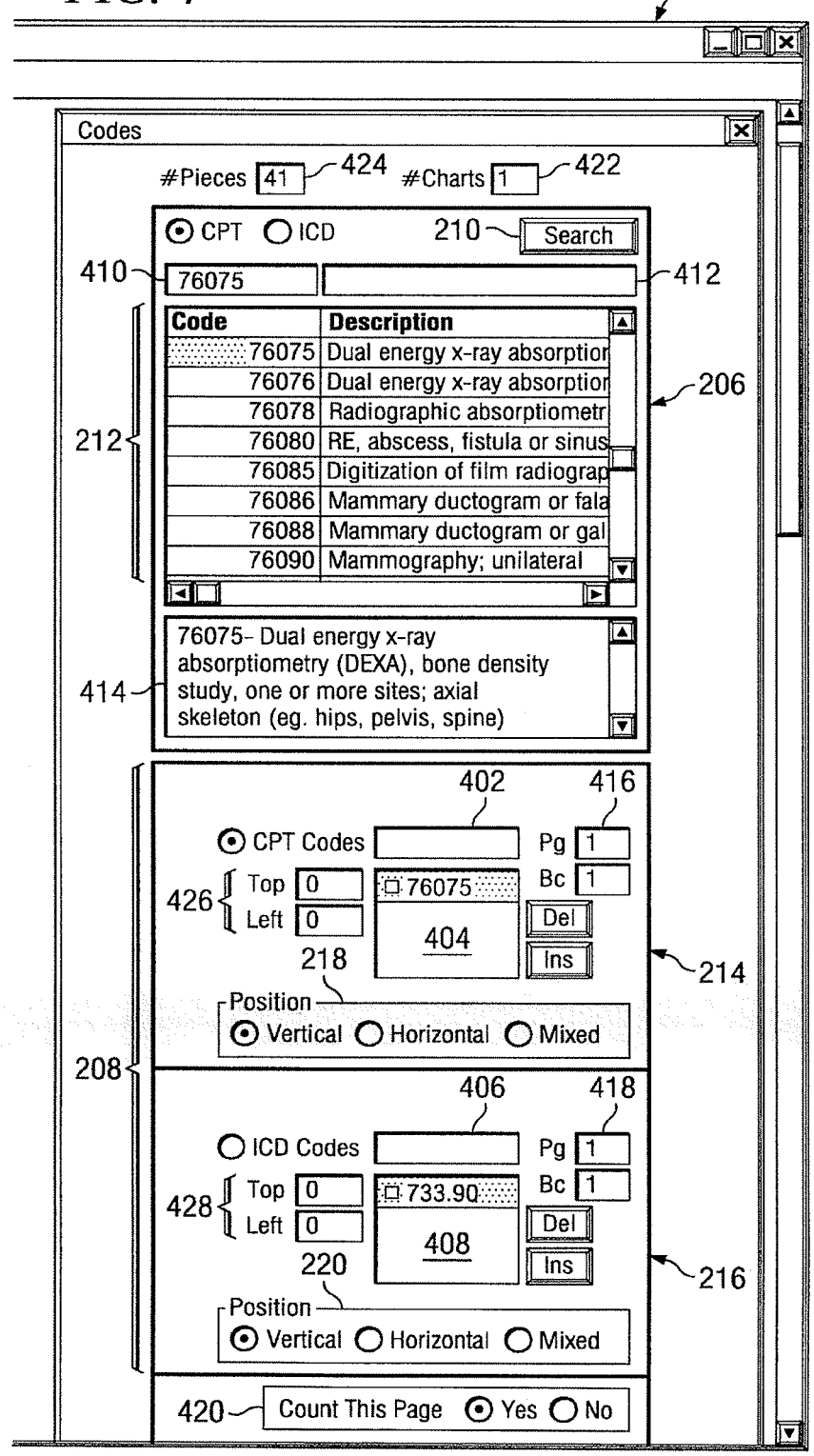
FIG. 4 illustrates various features of a medical-code area.

FIG. 4 illustrates various features of the medical-code area 204 in greater detail. As noted above relative to FIGS. 2-3, the medical-code area 204 may be used to perform a variety of functions. These functions included identification of medical codes to be added to a medical-chart image displayed in the imaging area 202, addition of the identified medical codes to the medical-chart image, and specification of where and in what format the medical codes are to be added to the medical-chart image. Various functions of the medical-code area 204 will now be described in further detail.

A CPT code assignment window 402 permits a medical-coding team member to assign a correct CPT code to be added to the medical-chart image. A CPT code added in the CPT code assignment window 402 is displayed in a CPT code display column 404. CPT codes displayed in the CPT code display column 404 may be deleted, modified, or inserted by the medical-coding team member. A displayed CPT code in the CPT code display column 404 may be bolded as shown in FIG. 4 in order to permit the medical-coding team member to browse a list of possible diagnosis codes (e.g., ICD codes) for the bolded CPT code. A pertinent diagnosis code (e.g., ICD code) may be assigned via an ICD code assignment window 406. An ICD code added in the ICD code assignment window 406 is displayed in an ICD code display column 408. The ICD codes shown in the ICD code display column 408 may be bolded, modified, inserted, or deleted in similar fashion to that described above with respect to CPT codes.

A code-number search window 410 of the free-text search facility 206 may be used by a medical-coding team member to search for either ICD or CPT codes from a stored list. A code-keyword search window 412 may also be used to search for ICD or CPT codes by typing keywords from the medical-chart image. A code description box 414 displays a code description for the selected code, regardless of whether the selected code is a CPT code or an ICD code. A CPT code tracker 416 tracks the number of CPT codes assigned per page and per batch. A Pg column of the CPT code tracker 416 provides the exact number of CPT codes entered in a particular medical-chart image page, while a Bc column of the CPT code tracker 416 adds the number of CPT codes entered on each medical-chart image page within a batch and displays the total number of CPT codes added to the batch as a whole. An ICD code tracker 418 operates in similar fashion to the CPT code tracker 416. A CPT position selector 218 permits a medical-coding team member to choose how the CPT codes are to be positioned on the medical-chart image. Thus, the medical-coding team member may add the CPT code onto the medical-chart image within a suitable space on the medical-chart image either vertically, horizontally, or in a mixed format. The ICD position selector 220 operates in similar fashion to the CPT position control 426.

Depending on the availability of space, the coder can choose where the medical codes are to be positioned. For example, a horizontal format may indicate that the codes are to be assigned one after the other separated by a comma. A vertical format may indicate that codes are to be assigned one below the other. In some charts, for example, a plurality of encounters may be segregated using a check mark and placed horizontally and aligned one below the other. A page counter control 420 permits a medical-coding team member to cause procedure and diagnosis codes assigned to the displayed medical-chart image to be counted responsive to selection of "Yes;" if "No" is selected, the displayed medical-chart image will be pulled. If a medical-chart image is a duplicate of a medical-chart image that has already been coded, the medical-chart image is marked to be pulled and not counted.

A chart counter window 422 tracks the number of medical-chart image pages that have been coded, the number of coded pages in turn providing details regarding how many patients have been coded, excluding pulled pages. A piece tracker window 424 tracks the number of pieces in the batch excluding a first-page header. A CPT position control 426 includes a top position window and a left position window. The CPT position control 426 allows a medical-coding team member to select, using Cartesian coordinates, where a CPT code is to be added to the medical-chart image. An ICD position control 428 operates in similar fashion to the CPT position control 426.

Figure 5:
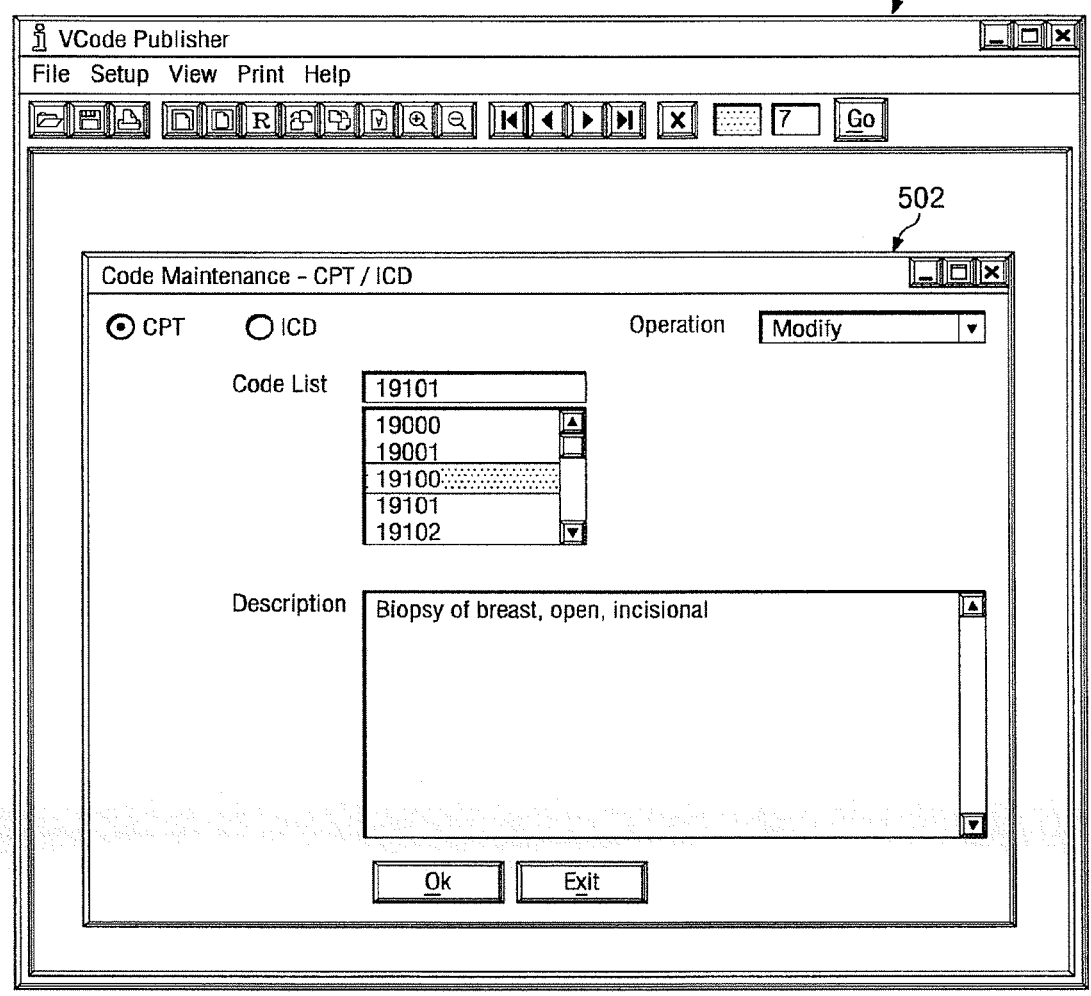
FIG. 5 illustrates a user interface including a code maintenance control.

FIG. 5 illustrates a user interface including a code maintenance control. A user interface 500 includes a code maintenance control 502. The code maintenance control 502 permits code descriptions and other information to be stored as part of the modified medical-chart image electronic file. The code maintenance control 502 also permits an added medical code or its description to be modified, added, or deleted. In a typical embodiment, the code and description, as well as any additional stored information, is registered and may be displayed from that point forward in the life of the medical-chart image to any medical-coding team member or other person viewing the medical-chart image as modified.

FIGS. 6A-B illustrate the user interface in a typical-use scenario. In FIGS. 6A-B, the user interface 200 displays a radiology report medical-chart image displayed in the imaging area 202. In a typical procedure, a medical-coding team member, when presented with the user interface 200 and the medical-chart image displayed on the imaging area 202 of the interface 200, typically initially notes the patient's age 602 and gender 604 as shown on the medical-chart image. The medical-coding team member then typically searches using the free-text search facility 206 for the term "mammogram." The search for the term "mammogram" would result in a CPT code of 76092 as shown in the CPT code display column 404. The medical-coding team member can then, responsive to noticing from the medical-chart image that the mammogram was a routine screening, input an ICD code of V76.12, which ICD code appears in the ICD code display column 408. A description of the CPT code 793.80 as an abnormal unspecified mammogram appears in the code description box 414.

Figure 7B:
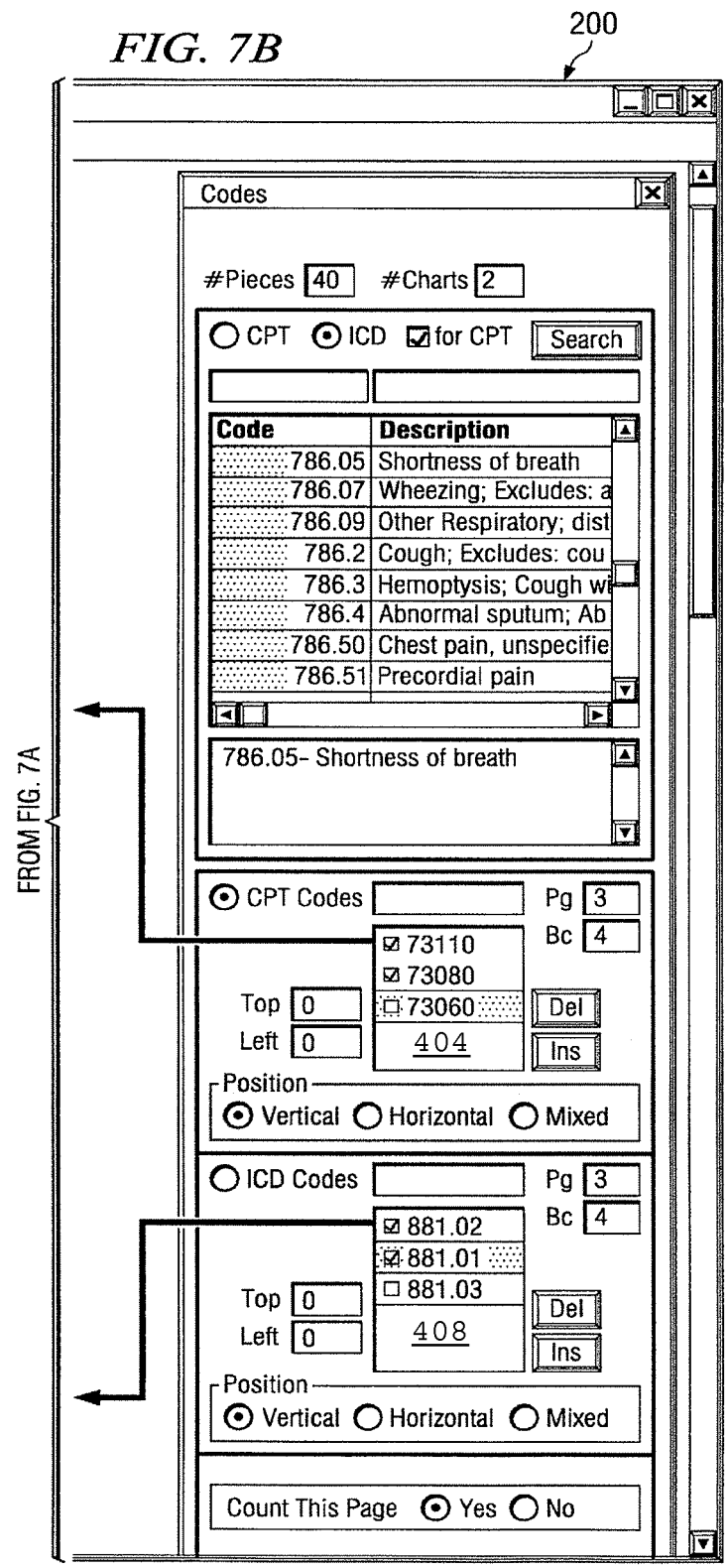

FIGS. 7A-B illustrate a user interface with medical codes added to a medical-chart image displayed therein. In the medical-chart image displayed in the imaging area 202, various medical codes have already been added. In an area 710, CPT codes 73110 and 73080 have been added in the mixed format. In similar fashion, ICD codes 881.02, 881.01, 881.03 have been added in an area 712. The tick marks beside the CPT codes and ICD codes in the CPT code display column 404 and the ICD code display column 408 respectively, indicate that the medical code following the tick mark is to be considered as a split encounter.

Figure 8A:
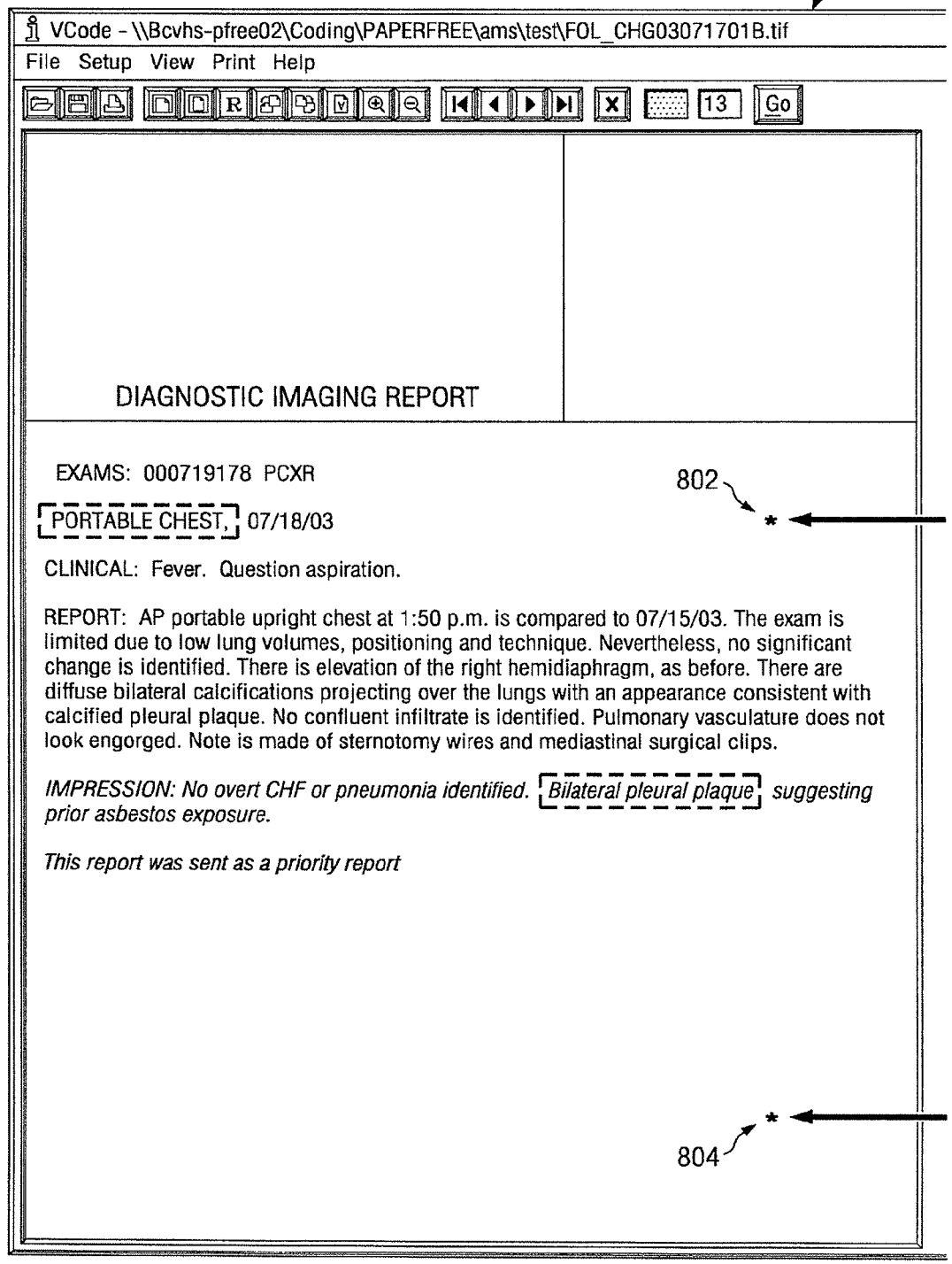
FIGS. 8A-B illustrate the user interface of FIGS. 2A-B after positions have been selected by a medical-coding team member for placement of medical codes on a medical-chart image.
Figure 8B:
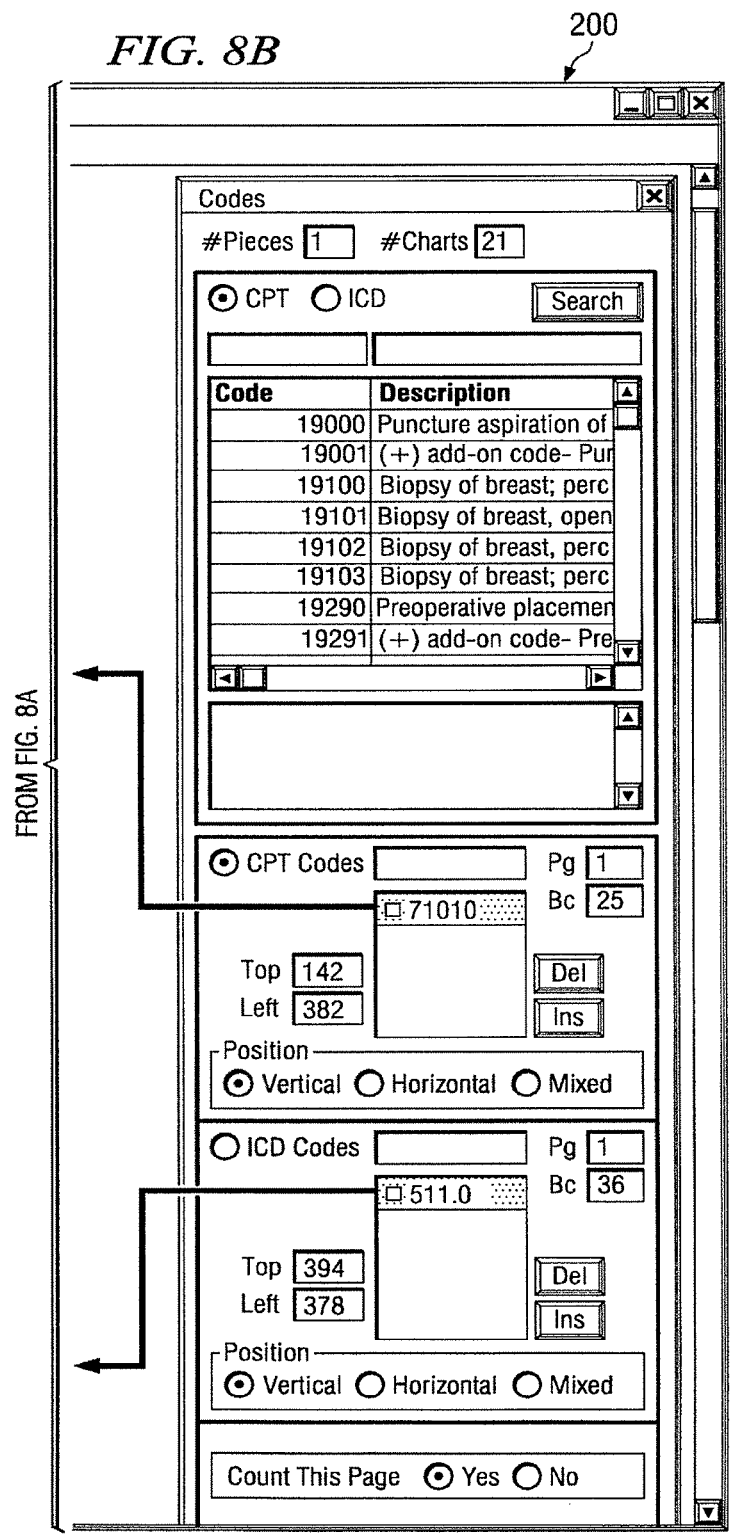

FIGS. 8A-B illustrate a user interface in which positions have been selected by a medical-coding team member for placement of medical codes on a medical-chart image. In the medical-chart image displayed in the imaging area 202, a position 802 and a position 804 are illustrated, each of the positions 802 and 804 being indicated by a star character and an arrow pointing from a CPT code and a corresponding ICD code. In a typical procedure, a medical-coding team member selects the position 802 at which position the CPT code 71010 is to be added to the medical-chart image. It will be apparent to those having skill in the art that the medical-coding team member has selected the position 802 as a position on the displayed medical-chart image in which no text currently appears. The position 804 is selected as the position at which the ICD code 511.0 is to be added. In a typical embodiment, a star in the position 802 and a star in the position 804 are of different colors in order to indicate to the medical-coding team member whether the CPT code or the ICD code is to be added at a given position. In a typical embodiment, the medical-coding team member can indicate the positions 802 and 804 merely by positioning a cursor and clicking a mouse at the desired position.

FIG. 9 illustrates a modified medical-chart image with medical codes added thereon by a medical-coding team member. As shown, the CPT code 76092, the ICD code 793.80, and the ICD code V76.12 have all been added in appropriate blank spaces of the medical-chart image.

Figure 10:
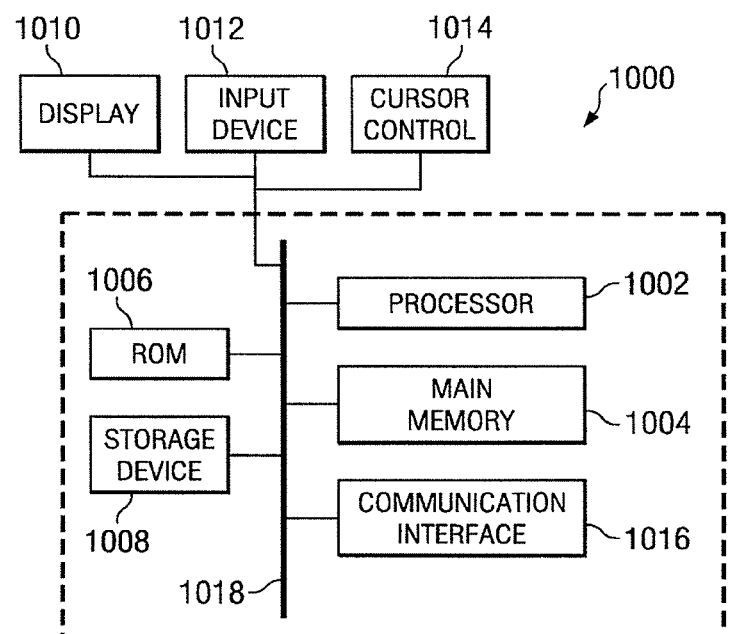
FIG. 10 illustrates an embodiment of a computer on which various embodiments of the invention may be implemented.

FIG. 10 illustrates an embodiment of a computer on which various embodiments of the invention may be implemented. In the implementation shown, a server 1000 may include a bus 1018 or other communication mechanism for communicating information and a processor 1002 coupled to the bus 1018 for processing information. The server 1000 also includes a main memory 1004, such as a random access memory (RAM) or other dynamic storage device, coupled to the bus 1018 for storing computer readable instructions to be executed by the processor 1002.

The main memory 1004 also may be used for storing temporary variables or other intermediate information during execution of the instructions to be executed by the processor 1002. The server 1000 further includes a read only memory (ROM) 1006 or other static storage device coupled to the bus 1018 for storing static information and instructions for the processor 1002. A computer readable storage device 1008, such as a magnetic disk or optical disk, is coupled to the bus 1018 for storing information and instructions for the processor 1002.

The server 1000 may be coupled via the bus 1018 to a display 1010, such as a cathode ray tube (CRT), for displaying information to a user. An input device 1012, including, for example, alphanumeric and other keys, is coupled to the bus 1018 for communicating information and command selections to the processor 1002. Another type of user input device is a cursor control 1014, such as a mouse, a trackball, or cursor direction keys for communicating direction information and command selections to the processor 1002 and for controlling cursor movement on the display 1010. The cursor control 1014 typically has two degrees of freedom in two axes, a first axis (e.g., x) and a second axis (e.g., y), that allow the device to specify positions in a plane.

The term "computer readable instructions" as used above refers to any instructions that may be performed by the processor 1002 and/or other component of the server 1000. Similarly, the term "computer readable medium" refers to any storage medium that may be used to store the computer readable instructions. Such a medium may take many forms, including, but not limited to, non volatile media, volatile media, and transmission media. Non-volatile media include, for example, optical or magnetic disks, such as the storage device 1008. Volatile media include dynamic memory, such as the main memory 1004. Transmission media include coaxial cables, copper wire and fiber optics, including wires of the bus 1018. Transmission media can also take the form of acoustic or light waves, such as those generated during radio frequency (RF) and infrared (IR) data communications. Common forms of computer readable media include, for example, a floppy disk, a flexible disk, hard disk, magnetic tape, any other magnetic medium, a CD ROM, DVD, any other optical medium, punch cards, paper tape, any other physical medium with patterns of holes, a RAM, a PROM, an EPROM, a FLASH EPROM, any other memory chip or cartridge, a carrier wave, or any other medium from which a computer can read.

Various forms of the computer readable media may be involved in carrying one or more sequences of one or more instructions to the processor 1002 for execution. For example, the instructions may initially be borne on a magnetic disk of a remote computer. The remote computer can load the instructions into its dynamic memory and send the instructions over a telephone line using a modem. A modem local to the server 1000 can receive the data on the telephone line and use an infrared transmitter to convert the data to an infrared signal. An infrared detector coupled to the bus 1018 can receive the data carried in the infrared signal and place the data on the bus 1018. The bus 1018 carries the data to the main memory 1004, from which the processor 1002 retrieves and executes the instructions. The instructions received by the main memory 1004 may optionally be stored on the storage device 1008 either before or after execution by the processor 1002.

The server 1000 may also include a communication interface 1016 coupled to the bus 1018. The communication interface 1016 provides a two-way data communication coupling between the server 1000 and a network, such as the card network of FIG. 1. For example, the communication interface 1016 may be an integrated services digital network (ISDN) card or a modem used to provide a data communication connection to a corresponding type of telephone line. As another example, the communication interface 1016 may be a local area network (LAN) card used to provide a data communication connection to a compatible LAN. Wireless links may also be implemented. In any such implementation, the communication interface 1016 sends and receives electrical, electromagnetic, optical, or other signals that carry digital data streams representing various types of information. The storage device 1008 can further include instructions for carrying out various processes for image processing as described herein when executed by the processor 1002. The storage device 1008 can further include a database for storing data relative to same.

The previous description is of embodiment(s) of the invention. The scope of the invention should not be limited by this description. The scope of the invention is instead defined by the following claims.

What is claimed is:

1. A method comprising:
   on a computer system comprising at least one server computer, maintaining a stored list of medical codes;
   for each electronic medical-chart image in a plurality of batches of electronic medical-chart images, the computer system allowing the electronic medical-chart image to be viewed and coded in a single software application, the allowing comprising:
      causing the electronic medical-chart image to be displayed in a first part of the single software application; and
      providing a search interface for searching the stored list of medical codes in a second part of the single software application;
      receiving, via the search interface, a search request based on information from the displayed electronic medical-chart image;
      locating at least one medical code in the stored list responsive to the search request;
      receiving identification of a selected medical code of the at least one medical code;
      receiving selection of a position on the displayed electronic medical-chart image at which the selected medical code is to be published;
      publishing the selected medical code, at the position, directly on the displayed electronic medical-chart image; and
      causing the published selected medical code to be displayed, at the position, directly on the displayed electronic medical-chart image; and
      saving the electronic medical-chart image with the published selected medical code as a modified electronic medical-chart image; and
   the computer system tracking a number of medical codes assigned per electronic medical-chart image and per batch.

2. The method of claim 1, wherein the list of medical codes comprises medical codes selected from the group consisting of ICD codes and CPT codes.

3. The method of claim 1, wherein the publishing step comprises publishing the selected medical code in a format selected from the group consisting of vertical, horizontal, and mixed.

4. The method of claim 1, wherein the received selection results from manual selection of the position on the displayed electronic image.

5. The method of claim 1, wherein the received selection results from specification of coordinates of the position on the displayed electronic medical-chart image.

6. An article of manufacture comprising:
   at least one non-transitory computer readable medium;
   processor instructions contained on the at least one computer-readable medium, the process instructions configured to be readable from the at least one computer-readable medium by at least one processor and thereby cause the at least one processor to operate as to:
   maintain a stored list of medical codes;
   for each electronic medical-chart image in a plurality of batches of electronic medical-chart images, allow the electronic medical-chart image to be viewed and coded in a single software application, the allowance comprising operability to:
      cause the electronic medical-chart image to be displayed in a first part of the single software application;
      provide a search interface for searching the stored list of medical codes in a second part of the single software application;
      receive, via the search interface, a search request based on information from the displayed medical-chart electronic image;
      locate at least one medical code in the stored list responsive to the search request;
      receive identification of a selected medical code of the at least one medical code;
      receive selection of a position on the displayed electronic medical-chart image at which the selected medical code is to be published;
      publish the selected medical code, at the position, directly on the displayed electronic medical-chart image; and
      cause the published selected medical code to be displayed, at the position, directly on the displayed electronic medical-chart image; and
   track a number of medical codes assigned per electronic medical-chart image and per batch.

7. The article of manufacture of claim 6, wherein the list of medical codes comprises medical codes selected from the group consisting of ICD codes and CPT codes.

8. The article of manufacture of claim 6, wherein the published selected medical code is published in a format selected from the group consisting of vertical, horizontal, and mixed.

9. The article of manufacture of claim 6, wherein the received selection results from manual selection of the position on the displayed electronic medical-chart image.

10. The article of manufacture of claim 6, wherein the received selection results from specification of coordinates of the position on the displayed electronic medical-chart image.

11. A system for adding information to a displayed electronic image, the system comprising:
    a server computer comprising a processor, wherein the server computer is operable to implement a method comprising:
    maintaining a stored list of medical codes;
    for each electronic medical-chart image in a plurality of batches of electronic medical-chart images, allowing the electronic medical-chart image to be viewed and coded in a single software application, the allowing comprising:

causing the electronic medical-chart image to be displayed in a first part of the single software application; and providing a search interface for searching the stored list of medical codes in a second part of the single software application;

receiving, via the search interface, a search request based on information from the displayed electronic medical-chart image;

locating at least one medical code in the stored list responsive to the search request;

receiving identification of a selected medical code of the at least one medical code;

receiving selection of a position on the displayed electronic medical-chart image at which the selected medical code is to be published;

publishing the selected medical code, at the position, directly on the displayed electronic medical-chart image; and causing the published selected medical code to be displayed, at the position, directly on the displayed electronic medical-chart image; and saving the electronic medical-chart image with the published selected medical code as a modified electronic medical-chart image; and tracking a number of medical codes assigned per electronic medical-chart image and per batch.

12. The system of claim 11, wherein the list of medical codes comprises medical codes selected from the group consisting of ICD codes and CPT codes.

13. The system of claim 11, wherein the selected medical code can be added in a format selected from the group consisting of vertical, horizontal, and mixed.

14. The system of claim 11, wherein the received selection results from manual selection of the position on the displayed electronic medical-chart image.

15. The system of claim 11, wherein the received selection results from specification of coordinates of the position on the displayed electronic medical-chart image.

* * * * *